United States Patent [19]
Nishio et al.

[11] Patent Number: 5,096,817
[45] Date of Patent: Mar. 17, 1992

[54] PROCESS FOR PRODUCING ANTIBIOTICS BU-3608 D AND BU-3608 E

[75] Inventors: Maki Nishio; Yosuke Sawada, both of Tokyo; Takeo Miyaki; Toshikazu Oki, both of Yokohama, all of Japan

[73] Assignee: Bristol-Myers Company, New York, N.Y.

[21] Appl. No.: 627,669

[22] Filed: Dec. 14, 1990

Related U.S. Application Data

[62] Division of Ser. No. 203,776, Jun. 7, 1988, Pat. No. 4,992,425.

[51] Int. Cl.$^5$ .................... C12P 19/60; C12R 1/03

[52] U.S. Cl. .................. 435/75; 435/252.3; 435/825; 536/17.9; 536/18.1

[58] Field of Search .............. 435/75, 825, 252.1, 435/252.3; 536/6.4, 17.9, 18.1

[56] References Cited

U.S. PATENT DOCUMENTS 4,870,165  9/1989  Oki et al. .................. 435/75
4,992,425  2/1991  Nishio et al. .................. 435/75

Primary Examiner—Herbert J. Lilling
Attorney, Agent, or Firm—Mollie M. Yang

[57] ABSTRACT

Disclosed herein are antibiotic BU-3608 D and E isolated from *Actinomadura hibisca*. These compounds are active antifungal agents.

1 Claim, 2 Drawing Sheets

1H-NMR OF BU-3608 E (400 MHz, DMSO-d6)

PROCESS FOR PRODUCING ANTIBIOTICS BU-3608 D AND BU-3608 E

CROSS REFERENCE TO RELATED APPLICATION

This application is a divisional of our co-pending application Ser. No. 07/203,776, filed June 7, 1988, now U.S. Pat. No. 4,992,425.

BACKGROUND OF THE INVENTION

The present invention relates to antibiotics BU-3608 D and BU-3608 E which are new components isolated from *Actinomadura hibisca*. These compounds are active as antifungal agents.

SUMMARY OF THE INVENTION

The present invention provides compounds having the formula I

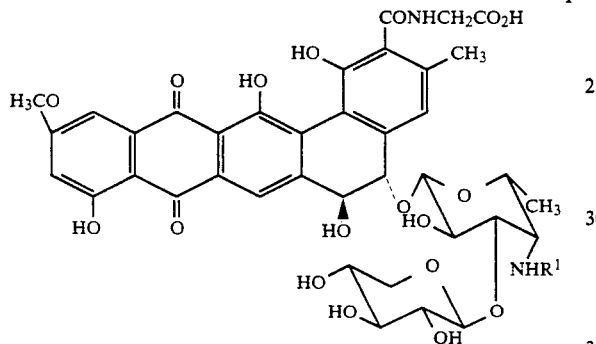

wherein $R^1$ is H or methyl; or a pharmaceutically acceptable salt thereof.

Another aspect of the invention provides a process for the production of an antibiotic of formula I which comprises culturing an antibiotic-producing strain of *Actinomadura hibisca*, preferably Strains P157-2 or Q278-4; and most preferably a mutant strain derived from Strain P157-2 herein designated as A2660.

DETAILED DESCRIPTION OF THE INVENTION

Antibiotics

The structures of antibiotics BU-3608 D and BU-3608 E are provided below as formulas II and III, respectively.

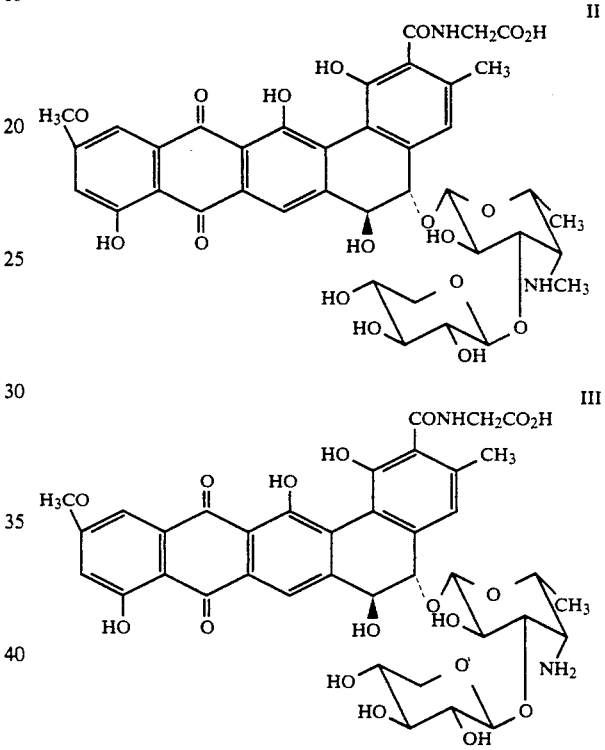

Figure 1:
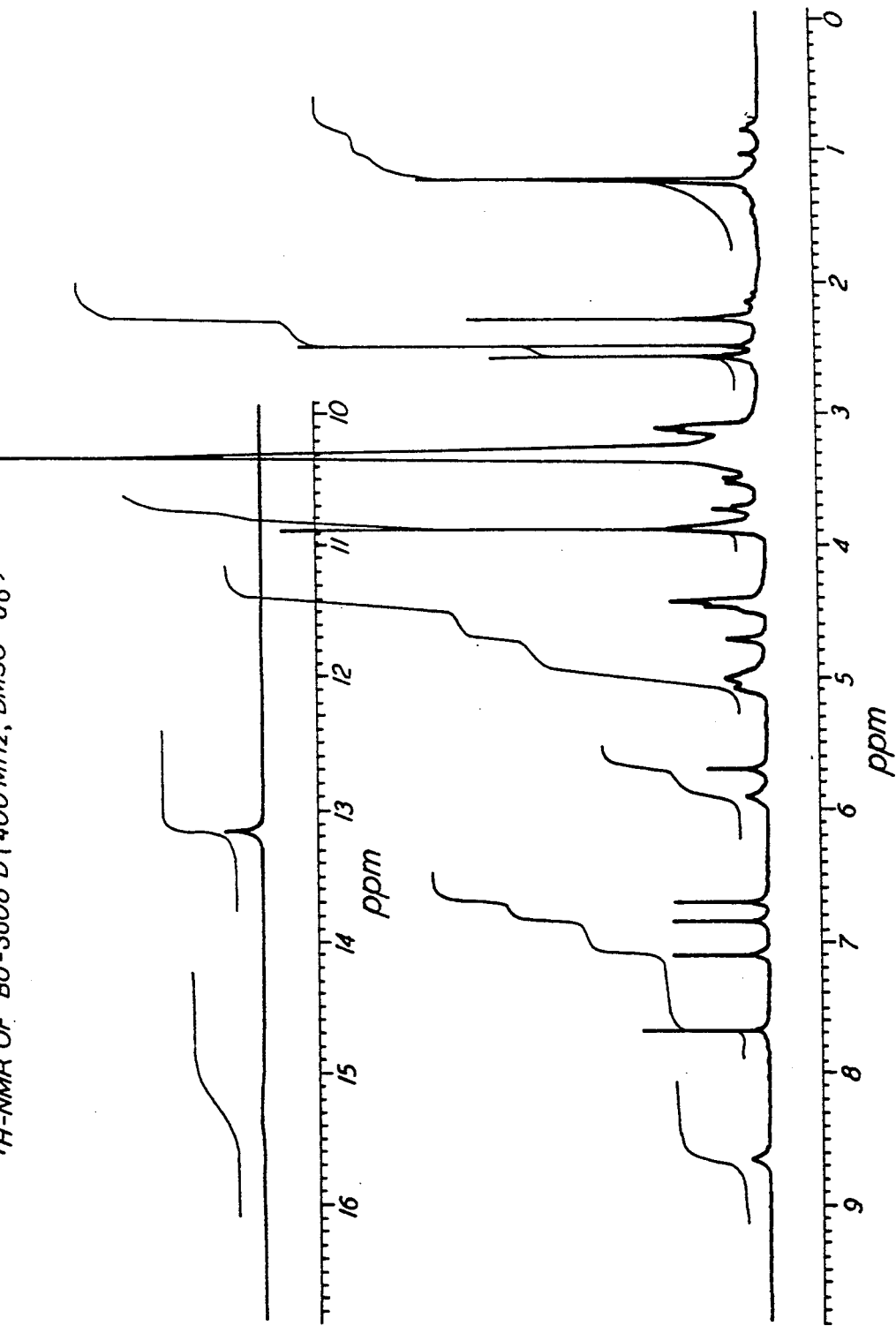
FIG. 1 represents a 400 MHz proton nuclear magnetic resonance spectrum of BU-3608 D.
Figure 2:
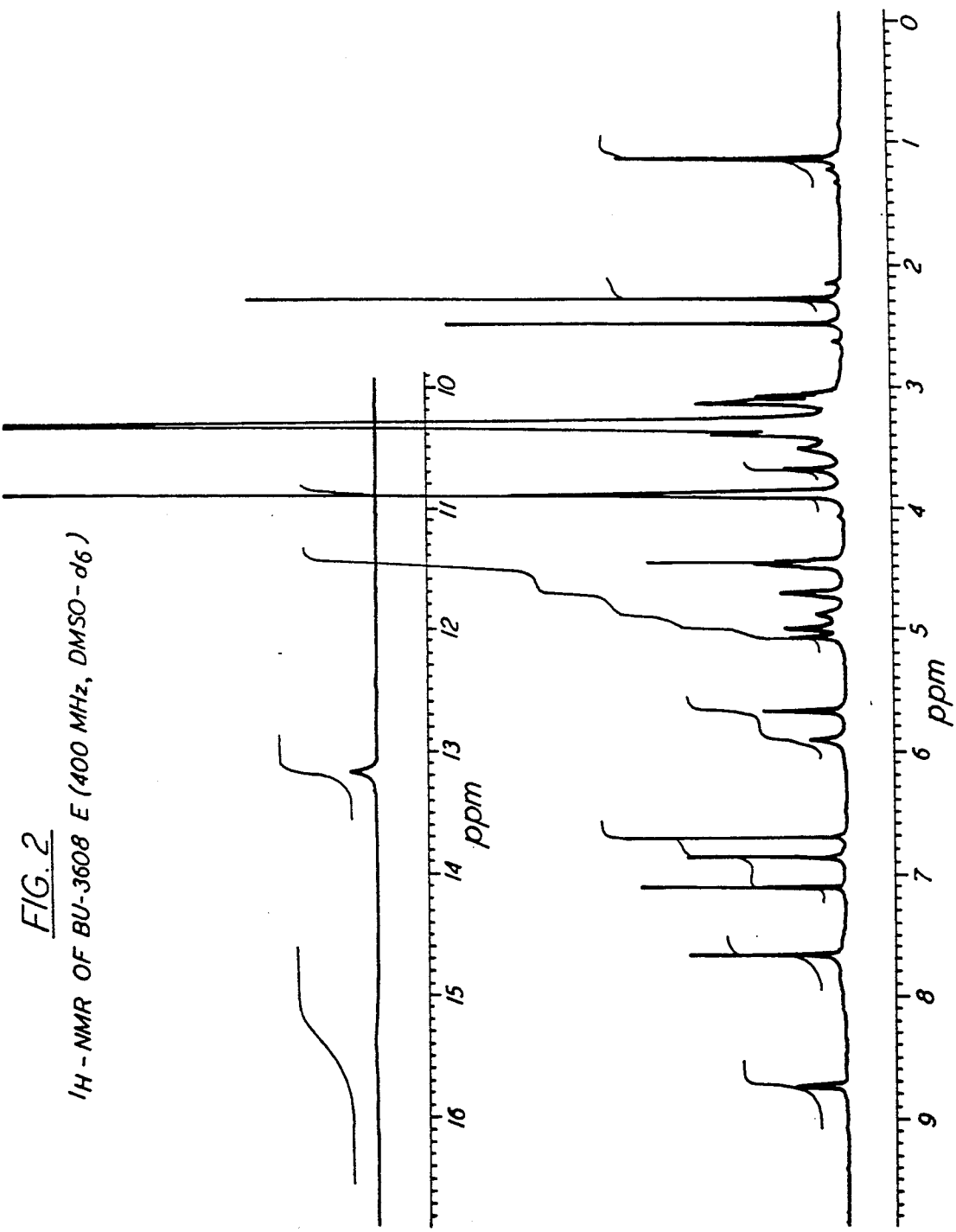
FIG. 2 represents a 400 MHz proton nuclear magnetic resonance spectrum of BU-3608 E.

Antibiotics BU-3608 D and BU-3608 E are characterized by the following physico-chemical properties:

|  | BU-3608 D | BU-3608 E |
|---|---|---|
| Nature: | Dark red amorphous powder | Dark red amorphous powder |
| M.P. (dec.): | 220–225° C. | 187–192° C. |
| $[\alpha]_D^{23}$: | +409° (c 0.1, 0.1N HCl) | +606° (c 0.1, 0.1N HCl) |
| SIMS m/z: | 827 (M + H)$^+$ | 813 (M + H)$^+$ |
| Molecular formula: | $C_{39}H_{42}N_2O_{18}$ | $C_{38}H_{40}N_2O_{18}$ |
| UV λmax nm (ε) in 50% MeOH: | 218(30,000), 280(23,600), 495(12,100) | 223(22,300), 280(18,700), 496(8,800) |
| in 0.01N HCl—50% MeOH: | 233(32,300), 298(28,500), 460(12,800) | 234(36,500), 298(31,700), 459(13,100) |
| in 0.01N NaOH—50% MeOH: | 240(31,000), 318(14,300), 500(14,500) | 240(32,900), 318(14,200), 500(14,900) |
| IR (KBr): | 3400, 2920, 1605, 1385, 1295, 1260, 1160, 1055 | 3380, 2900, 1605, 1385, 1295, 1255, 1160, 1040 |
| TLC SiO$_2$ Rf: (S-114, MeOAc-n-PrOH—28% NH$_4$OH = 45:105:60, v/v) | 0.16 | 0.14 |
| HPLC Rt (min): (ODS, CH$_3$CN—0.15% KH$_2$PO$_4$ pH 3.5 = 7:17) cf. BU-3608 A; 16.7, B; 21.8, C; 14.1 | 11.9 | 10.1 |
| $^1$H NMR: (400 MHz, DMSO-d$_6$) | substantially as shown in FIG. 1 | substantially as shown in FIG. 2 |
| $^{13}$C NMR: (100 MHz, DMSO-d$_6$) | 16.2 q — 20.0 q | 16.4 q — 20.1 q |

-continued

| BU-3608 D | BU-3608 E |
|---|---|
| 36.6 q | — |
| 41.0 t | 41.4 t |
| 55.8 q | 56.0 q |
| 63.1 d | 54.3 d |
| 65.7 t | 65.8 t |
| 68.2 d | 67.7 d |
| 69.3 d | 69.4 d |
| 70.0 d | 69.7 d |
| 71.6 d | 71.8 d |
| 73.5 d | 73.5 d |
| 75.8 d | 76.0 d |
| 80.9 d | 79.8 d |
| 81.9 d | 82.5 d |
| 104.0 d | 104.2 d |
| 104.0 d | 104.4 d |
| 105.0 d | 105.1 d |
| 105.7 d | 106.0 d |
| 110.2 s | 110.3 s |
| 111.4 d | 111.2 d |
| 116.6 d | 117.0 d |
| 118.7 s | 118.8 s |
| 118.9 s | 119.1 s |
| 126.0 s | 127.1 s |
| 131.7 s | 131.9 s |
| 132.7 s | 133.3 s |
| 136.5 s | 136.4 s |
| 137.4 s | 137.5 s |
| 137.8 s | 137.9 s |
| 143.3 s | 143.5 s |
| 158.1 s | 158.0 s |
| 163.7 s | 163.9 s |
| 165.6 s | 165.8 s |
| 165.7 s | 166.4 s |
| 168.7 s | 168.9 s |
| 171.1 s | 171.6 s |
| 179.9 s | 180.0 s |
| 187.1 s | 187.3 s |

The antibiotics of the present invention may be produced by cultivating an antibiotic producing strain of *Actinomadura hibisca* sp. nov. *Actinomadura hibisca* Strain No. P157-2 was isolated from a soil sample collected on Fiji Island in the South Pacific. A biologically pure culture of *Actinomadura hibisca* sp. nov. Strain No. P157-2 has been deposited with the American Type Culture Collection, Rockville, Md., and added to their permanent collection of microorganisms as ATCC 53557. Strain P157-2 produces BU-3608 as a major metabolite, and BU-3608 B, BU-3608 C, BU-3608 D, and BU-3608 E are co-produced as minor components. *Actinomadura hibisca* Strain No. Q278-4 was isolated from a soil sample collected in Andhra Pradesh State, India and this strain produces as major active components antibiotic BU-3608 and BU-3608 C, as well as BU-3608 B, BU-3608 D, and BU-3608 E as a minor components. A biologically pure culture of this microorganism has also been deposited with the ATCC, and assigned the accession number ATCC 53646. Both strains, however, produce the D and E components in very small amounts; each of D and E component comprises less than 1% of the total antibiotic production of either strain.

In an effort to increase the production of BU-3608 D and BU-3608 E mutation study of Strain P157-2 was initiated. *Actinomadura hibisca* Strain P157-2 was subject to chemical mutation using N-methyl-N'-nitro-N-nitrosoguanidine (NTG). From this work, a mutant strain designated as A2660 has been selected based on its consistent production of the antibiotic complex in which the ratio of D+E to A+C is much higher than that of the parent strain. *Actinomadura hibisca* P157-2 mutant strain A2660 has been deposited with the ATCC and assigned the accession number ATCC 53762.

It is to be understood that the present invention is not limited to use of the particular Strain P157-2 or Q278-4 or the mutant strain A2660 or to organisms fully answering the above description. It is especially intended to include other BU-3608 producing strains or mutants or variants of said organisms which can be produced from the described organisms by known means such as X-ray radiation, ultraviolet radiation, treatment with nitrogen mustard, phage exposure, and the like.

ANTIBIOTIC PRODUCTION

The antibiotics of the present invention are produced by cultivating *Actinomadura hibisca* Strain No. P157-2 or Strain Q278-4, or a mutant or a variant thereof such as strain A2660, in a conventional aqueous medium. The organism is grown in a nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate assimilable carbon source such as ribose, glucose, sucrose, cellobiose. As nitrogen source, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron, and the like.

Production of the antibiotic complex comprising BU-3608, and the B, C, D, and E components may be effected at any temperature conducive to satisfactory growth of the producing organism, e.g. 25°–40° C. and is most conveniently carried out at a temperature of around 27°–32° C. Ordinarily, optimum antibiotic production is obtained in shake flasks after incubation periods of 5–8 days. Aeration in shake flasks is achieved by agitation, e.g. shaking on a rotary shaker. If fermentation is to be carried out in tank fermentors, it is desirable to produce a vegetative inoculum in a nutrient broth by inoculating the broth culture from a slant culture or a lyophilized culture of the organism. After obtaining an active inoculum in this manner, it is aseptically transferred to the fermentation tank medium. Antibiotic production in tank fermentors usually reaches the optimum after 3–6 days of incubation. Agitation in the tank fermentor is provided by stirring and aeration may be achieved by injection of air or oxygen into the agitated mixture. Antibiotic production may be monitored using chromatographic or spectroscopic techniques, or by a conventional biological assay.

ISOLATION AND PURIFICATION OF ANTIBIOTICS

The antibiotics of the present invention may be recovered from the cultivated broth by any suitable method for such recovery. A general scheme for one such method for the isolation and purification of antibiotic BU-3608 from the fermentation broth of Strain P157-2 is shown below as Scheme I.

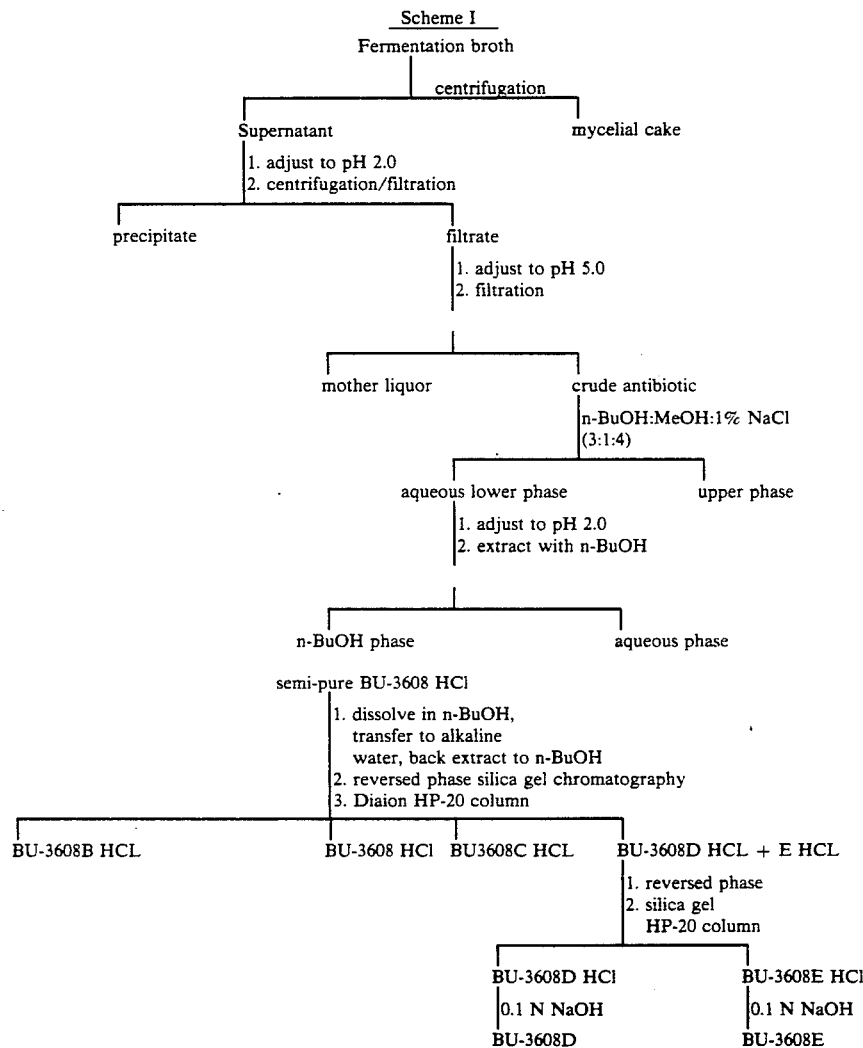

To elaborate on the flow chart of Scheme I, whole fermentation broth is separated into mycelial cake and supernatant by a conventional method such as centrifugation. The supernatant is acidified and the precipitate thus formed is removed. The filtrate is adjusted to pH 5 to deposit crude antibiotic which is collected and partitioned between an water immiscible organic solvent and an aqueous phase; an example of such a solvent system is n-butanol-methanol-1% NaCl mixture. The aqueous phase is separated, acidified, and extracted with an organic solvent such as n-butanol. The extract is concentrated in vacuo and lyophilized to yield semi-pure hydrochloride of BU-3608. This material contains BU-3608 as the major component and BU-3608 B, C, D, and E as minor components. These minor components may be separated from the semi-pure BU-3608 HCl by, for example, reversed phase silica gel chromatography. The D and E components thus isolated may be further purified by further chromatography steps as needed.

Detailed description of *Actinomadura hibisca* Strains P157-2 and Q278-4, of isolation and purification procedures of BU-3608, BU-3608 B, and BU-3608 C are given in our copending application U.S. Ser. No. 115,273, filed Nov. 2, 1987 which is hereby incorporated by reference.

BIOLOGICAL PROPERTIES

The antifungal activities of BU-3608 D and BU-3608 E were evaluated both in vitro and in vivo. The minimum inhibitory concentrations (MICs) against various fungi were determined by serial agar and broth dilution methods using Sabouraud dextrose agar and broth. The inoculum size of the test organism was adjusted to $10^6$ cells/ml in the broth dilution method. For the agar dilution method, approximately 0.003 ml of fungal suspension containing $10^6$ cells/ml was applied to the surface of agar plates containing the test antibiotics. The MIC values recorded after the cultures had been incubated for 44 hours at 28° C. are set forth below in Table I.

TABLE I

BU-3608 D and E in vitro antifungal activity in Sabouraud dextrose agar and broth.

| Test Organisms | | MIC (g/ml) | | | |
|---|---|---|---|---|---|
| | | BU-3608D | | BU-3608E | |
| | | AGAR | BROTH | AGAR | BROTH |
| *Candida albicans* | IAM4888 | 6.3 | — | 3.1 | — |
| " | A9540 | 6.3 | 12 | 6.3 | 12.5 |
| *Cryptococcus neoformans* | D49 | 1.6 | — | 0.8 | — |
| " | IAM4514 | 0.8 | — | 0.8 | — |
| *Asperillus fumigatus* | IAM2530 | 6.3 | — | 1.6 | — |
| " | IAM2034 | 6.3 | 12.5 | 6.3 | 12.5 |
| *Fusarium moniliforme* | A2284 | 6.3 | — | 12.5 | — |
| *Trichophyton mentagrophytes* | D155 | 3.1 | — | 12.5 | — |
| " | #4329 | 6.3 | 6.3 | 12.5 | 12.5 |
| *Sporothrix schenckii* | IFO8158 | 1.6 | — | 6.3 | — |
| *Asperillus flavus* | FA21436 | 3.1 | — | 6.3 | — |
| *Blastomyces dermatitidis* | D40 | 6.3 | — | 3.1 | — |
| *Petriellidium boydii* | IFO8073 | 25 | — | >100 | — |
| *Mucor spinosus* | IFO5317 | >100 | — | >100 | — |

In vivo activity of BU-3608 E was tested against *Candida albicans* A9540 infection in mice. Test organisms were cultured for 18 hours at 28° C. in YGP medium (yeast extract, glucose, peptone, $K_2HPO_4$, $MgSO_4$) and then suspended in saline. Male ICR mice weighing 20 to 24 g were infected intravenously with about 10 times the median lethal dose of the test fungus. The antibiotic at various dose levels was administered to groups of 5 mice each intravenously just after the fungal infection. The dose that protects 50% of the animals from infection (PD$_{50}$, mg/kg) was calculated from survival rates recorded on the 20th day after the fungal challenge. All control animals died within 7 to 15 days after infection. Results of the in vivo studies for BU-3608 E are shown in Table II. The PD$_{50}$ for BU-3608 D against the same organism and using the same test protocol as described above is 9 mg/kg/inj.

TABLE II

In Vivo Antifungal Activity Against *C. albicans* A9540 Intravenous Infections in Mice.

| Compound | Dose* | Number of survivors/tested |
|---|---|---|
| BU-3608 E | 50 | 5/5 |
| | 25 | 5/5 |

TABLE II-continued

In Vivo Antifungal Activity Against *C. albicans* A9540 Intravenous Infections in Mice.

| Compound | Dose* | Number of survivors/tested |
|---|---|---|
| | 12.5 | 4/5 |
| | 6.3 | 1/5 |
| | 3.1 | 0/5 |
| | 1.6 | 0/5 |
| PD$_{50}$ (mg/kg/inj.): | | 8.9 |

*Dose in mg/kg/inj.

The acute toxicity of BU-3608 D was determined in mice after single intraveneous administration. LD$_{50}$ was 210 mg/kg.

For treatment of fungal infections in animals and human beings, the antibiotics of the present invention may be given in an antifungally effective amount by any accepted routes of administration; these include, but are not limited to, intravenous, intramuscular, oral, intranasal, and for superficial infections, topical administration. Preparations for parenteral administration include sterile aqueous or non-aqueous solutions, suspensions or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that when treating a host infected with a fungus susceptible to the antibiotics of this invention, the actual preferred route of administration and dosage used will be at the discretion of the attending clinician skilled in the treatment of fungal or viral infections, and will vary according to the causative organism, its sensitivity to the antibiotic, severity and site of the infection, and patient characteristics such as age, body weight, rate of excretion, concurrent medications, and general physical condition.

The following examples are illustrative without limiting the scope of the present invention.

EXAMPLE 1

Fermentation of *Actinomadura hibisca* Strain P157-2

(a) Agar slant. *Actinomadura hibisca* strain P157-2 was grown on a agar slant consisting of
  0.5% soluble starch (Nichiden Kagaku Co.)
  0.5% glucose
  0.1% fish meat extract (Mikuni Kagaku)
  0.1% yeast extract (Oriental Yeast Co.)
  0.2% NZ case (Sheffield)
  0.1% $CaCO_3$
  0.2% NaCl
  1.6% agar The culture was incubated at 28° C. for 7 days.

(b) Seed culture. A portion of the microbial growth from the slant culture was transferred to a 500 ml Erlenmeyer flask containing 100 ml of vegetative medium of the following composition:
  1.0% glucose
  2.0% soluble starch (Nichiden Kagaku Co.)
  0.5% NZ amine A (Sheffield)
  0.5% yeast extract (Oriental Yeast Co.)
  0.1% $CaCO_3$ The pH of the medium was adjusted to 7.2 before sterilization. The seed culture was incubated at 28° C. for 4 days on a rotary shaker set at 200 rev. per minute.

(c) Flask fermentation. 5 ml of the microbial growth was transferred from the seed culture to a 500 ml Erlenmeyer flask containing 100 ml of sterile production medium of the following composition:
  3.0% glucose
  3.0% soybean meal (Nikko Seiyu Co.)
  0.5% Pharmamedia (Traders Protein)
  0.1% yeast extract (Oriental Yeast Co.)
  0.3% $CaCO_3$ The fermentation was carried out at 28° C. for 5 to 6 days on a rotary shaker. Antibiotic production in the fermentation broth was monitored by broth dilution method using *Candida albicans* A9540 as the indicator organism in Sabouraud dextrose broth; UV assay at 500 nm in 0.01N NaOH-MeOH (1:1) solution was also used. Antibiotic production reached a maximum at 650 μg/ml on day 5.

(d) Tank fermentation. 3 l of the seed culture was used to inoculate 120 l of sterile production medium contained in a 200 l tank fermentor. The composition of the production medium is the same as that used in flask fermentation. The tank was operated at 28° C. with the agitation rate set at 250 rev. per minute and the aeration rate at 120 l per minute. After 96 hrs of fermentation, an antibiotic potency of 500 μg/ml was obtained, and the pH of the broth was 7.9.

EXAMPLE 2

Isolation and Purification of Antibiotics

Detailed description for the isolation and purification of antibiotics BU-3608, BU-3608 B, and BU-3608 C is given in our co-pending application U.S. Ser. No. 115,273 filed Nov. 2, 1987 which is hereby incorportated by reference. The procedure for arriving at a crude sample of BU-3608 HCl containing as minor components BU-3608 B, C, D, and E is briefly described.

Harvested broth (pH 7.8) was centrifuged and the supernatant was acidified to pH 2.0 with 6N HCl to deposit bio-inactive solid. After the precipitate was removed, the filtrate was adjusted to pH 5.0 with 6N NaOH and the solution was stirred gently for 30 minutes at room temperature. The resultant dark red solid was filtered off and dried in vacuo. This solid was dissolved in a 3:1:4 mixture of n-butanol-methanol-1% NaCl and the mixture was stirred for 30 minutes. The lower aqueous layer was separated, washed again with fresh upper layer, acidified to pH 2.0 with 6N HCl, and then extracted with n-butanol. The n-butanol extract was washed with water, concentrated in vacuo and lyophilized to yield semi-pure BU-3608 hydrochloride. A solution of the solid in n-butanol was shaken with alkaline water (pH 9.0). The aqueous layer was acidified to pH 2.0 and washed with ethyl acetate. Extraction with n-butanol followed by evaporation of the solvent gave a purer sample of BU-3608 HCl. This material was then subjected to reversed phase silica gel chromatography (ODS-60, 350/250 mesh, Yamamura Chemical Lab., column 4.5×90 cm). The sample was dissolved in water and applied on the column which had been equilibrated with a mixture of acetonitrile-0.15% $KH_2PO_4$ (pH 3.5)=17:83 (v/v). The column was washed sequentially with 5 l each of acetonitrile-0.15% $KH_2PO_4$ mixture of the following ratios: 17:83, 18:82, 19:81, 20:80, and then developed with the same solvent mixture of a 22:78 ratio. The eluate was collected in 100 ml fractions which were monitored by the microplate assay using *C. albicans* A9540 and thin-layer chromatography ($SiO_2$, methyl acetate-n-propanol-28% ammonium hydroxide=45:105:60 v/v). The fractions containing the main homogeneous compound were combined and further purified to yield BU-3608. Fractions eluting before and after the main homogeneous fraction were collected and further purified to give BU-3608 C and BU-3608 B, respectively.

In the reversed phase silica gel chromatography procedure described above, fractions eluting before BU-3608 C were separately collected and pooled. The pooled pale orange-colored fraction were desalted using Diaion HP-20 chromatography. The solid thus obtained contained relatively enriched in the D and E components but still contained a large amount of the C component. The pooled solids (128 mg from a total of 60 l of fermentation broth) was charged on a column of reversed phase silica gel (ODS-60, Yamamura Chem. Lab., Φ 8.0×90 cm), and eluted with a 21:79 mixture of acetonitrile-0.15% $KH_2PO_4$ (pH 3.5). The eluate was examined by HPLC using a Microsorb Short One $C_{18}$ column (Rainin Instrument Co., 4.6 mm I.D.×100 mm, 3 μm), a 7:17 mixture of acetonitrile-0.15% $KH_2PO_4$ (pH 3.5) as the mobile phase at a flow rate of 1.2 ml/min., and UV absorption at 254 nm for detection. BU-3608 E eluted first followed by BU-3608 D. Fractions containing BU-3608 E were pooled, concentrated in vacuo and desalted by HP-20 chromatography to yield nearly homogeneous BU-3608 E HCl. An aqueous solution of BU-3608 E HCl was adjusted to pH 5.0 with 0.1N NaOH to deposit pure BU-3608 E as the zwitterion (13 mg). In a similar fashion, BU-3608 D as the zwitterion (4 mg) was obtained.

The isolation and purification procedure described above can be applied for isolating components D and E from the culture broths of mutant strains.

EXAMPLE 3

Mutation of *Actinomadura hibisca* Strain P157-2

Spores of *Actinomadura hibisca* Strain P157-2 (ATCC 53557) grown at 28° C. for 10 days on a modified Bennett's agar medium (soluble starch 0.5%, glucose, 0.5%, fish meat extract 0.1%, yeast extract 0.1%, NZ-case 0.2%, NaCL 0.2%, CaCO₃ 0.1% and agar 1.6%; pH 7.0) were suspended in saline, sonicated for 20 seconds at 0° C., harvested by centrifugation at 5,000 rpm for 10 minutes at 25° C., and resuspended it in 10 mM Tris-HCl (pH 9.0). The spore suspension was mixed with a solution of NTG (5,000 μg/ml) in 10% (v/v) dimethyl sulfoxide and the mixture was gently shaken for 1 hour at 28° C. The NTG-treated spores were harvested by centrifugation, resuspended in saline, spread on a new agar plate, and then incubated for 7 days at 28° C. Each colony was transferred to a vegetative medium (10 ml) consisted of glucose 3%, soybean meal 3%, Pharmamedia 0.5%, yeast extract 0.1%, and CaCO₃ 0.3% (pH 7.0) and the culture was incubated at 28° C. for six days on a shaker operating at 200 rpm. The antibiotic components produced in the fermentation broth were identified using silica gel TLC and HPLC. The mutant strain A-2660 was selected as the organism for larger-scale production of antibiotics BU-3608 D and E based on its ability to produce good amount of the D and E components relative to the A and C components, as well as its ability to produce the new antibiotics consistently. The ratios of antibiotic components produced by the parent P157-2 strain and the mutant strain A2660 are compared in the following Table.

| Strain | Total production (μg/ml) | Ratio of components[2] | | | |
|---|---|---|---|---|---|
| | | A | C | D | E |
| P157-2[1] | 780 | 84% | 7 | 0.5 | 0.2 |
| P157-2-A2660[1] | 550 | 35 | 21 | 22 | 19 |

[1]Medium: glucose 3%, soybean meal 3%, Pharmamedia 0.5%, yeast extract 0.1%, CaCO₃ 0.3%, pH 7.0 before autoclaving.
[2]Determined by HPLC using Waters M600, YMC-A301-3 system, and a 3:1 mixture of 0.15% potassium phosphate buffer-acetonitrile (pH 3.5) as solvent, with detection at 254 nm.

A portion of the microbial growth from the slant culture of the mutant strain was inoculated in 100 ml of modified Bennett's liquid medium (same composition as the agar medium except the agar therein was omitted) in a 500 ml Erlenmeyer flask and incubated at 28° C. for 4 days on a rotary shaker operating at 200 rpm. Five ml of the culture was transferred to a 500 ml-Erlenmeyer flask containing 100 ml of fresh medium and the fermentation was carried out on a rotary shaker at 28° C. for 6 days.

We claim:

1. A process for producing a compound of the formula

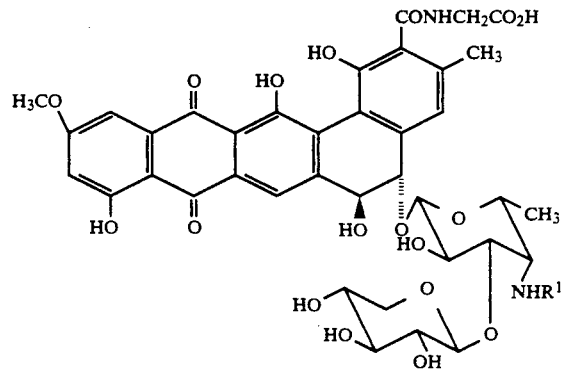

wherein R¹ is H or methyl, or a pharmaceutically acceptable salt thereof, which comprises cultivating an antibiotic producing strain of *Actinomadure hibisca* which is ATCC 53762 in a medium containing assimilable sources of carbon and nitrogen under aerobic conditions, and recovering said antibiotic from the cultured broth.

* * * * *